United States Patent [19]
Mager et al.

[11] Patent Number: 5,480,459
[45] Date of Patent: Jan. 2, 1996

[54] OXIDATIVE HAIR DYE BASED ON A CREAMLIKE CARRIER COMPOSITION AS WELL AS PROCESS FOR THE DYEING OF HAIR

[75] Inventors: Herbert Mager, Marly; Gilbert Pasquier, Praroman, both of Switzerland; Dieter Hoch, Pfungstadt-Eich, Germany; Johann Aeby, Marly, Switzerland

[73] Assignee: Wella Aktiengesellschaft, Darmstadt, Germany

[21] Appl. No.: 150,210

[22] PCT Filed: Apr. 6, 1993

[86] PCT No.: PCT/EP93/00848

§ 371 Date: Dec. 9, 1993

§ 102(e) Date: Dec. 9, 1993

[87] PCT Pub. No.: WO93/23006

PCT Pub. Date: Nov. 25, 1993

[30] Foreign Application Priority Data

May 18, 1992 [DE] Germany ............... 42 16 381.1

[51] Int. Cl.⁶ .................................................. A61K 7/13
[52] U.S. Cl. ................... 8/408; 8/406; 8/407; 8/409; 8/410; 8/412; 8/435
[58] Field of Search ..................... 8/405, 406, 407, 8/408, 410, 411, 412, 414, 415, 416, 421, 435, 409; 424/70

[56] References Cited

U.S. PATENT DOCUMENTS

| | | | |
|---|---|---|---|
| 4,295,848 | 10/1981 | Grollier et al. | 8/410 |
| 4,401,664 | 8/1983 | Scheuffgen | 424/365 |
| 4,425,132 | 1/1984 | Grollier et al. | 8/405 |
| 4,725,282 | 2/1988 | Hoch et al. | 8/405 |
| 4,754,069 | 6/1988 | Braun et al. | 8/410 |
| 5,100,656 | 3/1992 | Lang et al. | 424/70 |
| 5,106,609 | 4/1992 | Bolich, Jr. et al. | 8/405 |

FOREIGN PATENT DOCUMENTS

| | | |
|---|---|---|
| 0166100 | 2/1986 | European Pat. Off. |
| 3834142 | 12/1990 | Germany |
| 4017718 | 5/1991 | Germany |
| 2018302 | 10/1979 | United Kingdom |
| 9301792 | 4/1993 | WIPO |

OTHER PUBLICATIONS

"Cosmetics, Science And Technology", E. Sagarin, 1957, p. 503 ff.
"Handbook Of Cosmetics And Fragrances", (Handbuch der Kosmetika und Riechstoffe, H. Janystin, 1973, p. 338 ff.
Bohlin Instruments Information Sheets, "Bohlin Rheometer CS", Aug. 1993, pp. 1 to 6.
Colour Index, 3rd Edition, vol. 4, 1971, pp. 4053, 4070, 4389, 4537 and 4557.

Primary Examiner—Paul Lieberman
Assistant Examiner—Caroline L. Dusheck
Attorney, Agent, or Firm—Michael J. Striker

[57] ABSTRACT

The oxidative hair dye composition is in the form of a cream and contains a carrier substance and a dye mixture dissolved in it. The dye mixture includes at least one coupler and at least one developer. The composition has a pH between 4.5 to 12.5 and, in addition to the dye mixture, contains (A) 10 to 30 percent by weight of at least one fatty alcohol with 10 to 24 carbon atoms; (B) 0.2 to 6.0 percent by weight of at least one diester of formula (I)

$$R_1-CO-O-(CH_2-CH_2-O)_n-CO-R_2 \qquad (I),$$

where n is 1, 2 or 3, and $R_1$ and $R_2$ are each independently selected from the group consisting of alkyl groups with 12 to 20 carbon atoms; (C) 0.5 to 20 percent by weight glycerin fatty acid ester with 10 to 24 carbon atoms, and (D) 0.1 to 10 percent by weight of at least one emulsifier member selected from the group consisting of nonionic emulsifiers, anionic emulsifiers and ampholytic emulsifiers. The total content of fatty alcohol, of diester and of glycerin fatty acid ester is from 25.0 to 56.0 percent by weight.

10 Claims, No Drawings

OXIDATIVE HAIR DYE BASED ON A CREAMLIKE CARRIER COMPOSITION AS WELL AS PROCESS FOR THE DYEING OF HAIR

BACKGROUND OF THE INVENTION

The present invention relates to oxidation hair dyes and methods of dyeing hair using them.

Oxidative hair dye compositions in the form of creams have gained considerable importance in hair dyeing practice. Such hair dye compositions generally contain p-substituted benzene derivatives such as 2,5-diaminotoluene, 4-aminophenol 1,4-diaminobenzene, 2-(2'-hydroxyethyl)-1,4-diaminobenzene and 4-amino-N-(2'-mesylaminoethyl)aniline as well as 2,5-diaminoanisole, 2,5-diaminobenzyl alcohol, and tetraaminopyrimidine as oxidizing dyestuffs. The latter are known as developers. The developers are used in combination with suitable couplers. Such couplers include 1-naphthol, resorcinol, 4-chlororesorcinol, m-aminophenol, 5-amino-o-cresol and derivatives of m-phenylenediamine such as 2-amino-4-(2'-hydroxyethylamino)anisole. A wide assortment of different shades can be produced by a suitable combination of developers and couplers.

Oxidative hair dye compositions include two components which are mixed together shortly before use in a ratio of 1:1 and then applied to the hair to be dyed. One component, the dye carrier, contains the dye mixture and can take the form of a solution, gel or preferably a cream. The other component is usually in the form of a liquid or cream and contains a suitable oxidizing agent, e.g. hydrogen peroxide.

The dyeing takes place in the shaft of the hair by the reaction of the developers and couplers in the presence of an oxidizing agent.

In hair dyeing practice, highly-viscous dye carrier substances based on fatty alcohols are preferred when using mixtures of two components in the form of cream and in subsequent application with a brush. However, they have the disadvantage that they continue to thicken when stored so that it is considerably more difficult to remove them from the tube and mixing with the components containing the oxidizing ingredient requires more time. Moreover, conventional dye carrier substances in the form of cream tend to become "stringy" when removed from the tube, which makes handling more difficult.

The highly-viscous dye emulsion systems used in practice are very difficult to handle in technical production-related respects.

This is demonstrated during the production process, for example, in that the emulsion is first formed at relatively low temperatures so that the emulsion concentrates which can be diluted subsequently with cold water can be produced only with difficulty if at all.

An oxidizing hair dye composition in cream form having good stability when stored and a high dye/electrolyte content is known from the German Offenlegungsschrift or Published Patent Application 3 834 142, which concerns a low-viscosity preparation with a large number of ingredients. In addition to fatty alcohols and fatty acid esters, the composition contains a fatty acid monoethanolamide, lauryl alcohol ethoxylated with 2 moles ethylene oxide, and certain emulsifiers. Compositions of this type are preferably applied with the use of a shaker bottle. Accordingly, they cannot be applied by the users of the hair dye themselves. There is a risk with low-viscosity hair dye compositions that they can run off the hair because of reduced adherence to the hair.

SUMMARY OF THE INVENTION

The object of the present invention is therefore to provide a new oxidizing hair dye composition of high viscosity in the form of a cream which stores well and is simple to use in comparison with conventional oxidizing hair dye compositions in the form of cream. In addition, production of the highly-viscous dye carrier substance is facilitated by a simple formula.

It has now been found that the proposed object is met in an outstanding manner by a composition for the oxidative dyeing of hair in the form of a cream which contains a carrier substance and a dye mixture which is dissolved in the latter, characterized in that it contains (A) 10 to 30 percent by weight of at least one fatty alcohol with 10 to 24 carbon atoms, (B) 0.2 to 6.0 percent by weight of at least one diester of the following formula

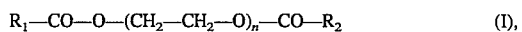

$$R_1-CO-O-(CH_2-CH_2-O)_n-CO-R_2 \qquad (I),$$

where n is 1, 2 or 3, and $R_1$ and $R_2$ represent identical or different alkyl groups with 12 to 20 carbon atoms, (C) 0.5 to 20 percent by weight glycerine fatty acid ester with 10 to 24 carbon atoms, (D) 0.1 to 10 percent by weight nonionic and/or anionic and/or ampholytic emulsifiers, and (E) has a pH of 4.5 to 12.5.

The new oxidizing hair dye compositions contain the fatty alcohols with 10 to 24 carbon atoms, e.g. cetyl stearyl alcohol, as thickeners. The preferred amount of fatty alcohol is 15 to 25 percent by weight.

Formula (I) contains ethylene glycol distearate as preferred diester.

The preferred quantity of glycerin fatty acid ester is 0.5 to 10.0 percent by weight. Glycerin monodistearate in particular, preferably with a content of 30 to 35 percent by weight monoester, is contained as glycerin fatty acid ester.

The total content of the fatty alcohol of component (A) acting as thickener and the fatty acid esters of components (B) and (C) is preferably 25.0 to 56.0 percent by weight.

Conventional nonionic, anionic and ampholytic emulsifiers are used as emulsifiers, for example: fatty alcohol sulfates, highly ethoxylated fatty alcohols, fatty alcohol ethane sulfonic acid salts, cholesterol, betaine-type zwitterionic emulsifiers, and preferably fatty alcohol ether sulfates, preferably in quantities of 2 to 5 percent by weight. The principle emulsifier with respect to quantity is preferably sodium lauryl alcohol diglycol ether sulfate.

Further, petrolatum, fatty acids, e.g. oleic acid and ethoxylated nonylphenols, can be contained as additional thickeners in quantities of 1.0 to 9.0 percent by weight.

Moreover, the oxidizing hair dye component can contain additional ingredients conventional for such compositions such as cationic resins in quantities of 0.05 to 1.0 percent by weight; solvents, e.g. ethanol, isopropanol, glycerin, 1,3-butanediol and propylene glycol in quantities of 1.0 to 5.0 percent by weight; antioxidants in quantities of 0.01 to 0.2 percent by weight; perfume oils in quantities of 0.01 to 1.0 percent by weight, and complexing agents for heavy metals in quantities of 0.01 to 0.5 percent by weight.

The oxidizing hair dye component is preferably free of alkylolamides and low-ethoxylated fatty alcohols such as lauryl alcohol ethoxylated with 2 moles ethylene oxide.

Depending on the composition, the hair dye composition according to the invention can be adjusted so as to be slightly acidic, neutral or alkaline. In particular, it has a pH of 4.5 to 12.5 and is preferably adjusted with ammonia.

The dyestuff mixture contained in the oxidizing hair dye composition has at least one coupler and at least one developer and, if necessary, also self-coupling dye precursors and dyes which are directly absorbed in the hair.

The developers and couplers are used in the hair dye compositions either as such or in the form of their physiologically unobjectionable salts with inorganic or organic acids, e.g. chloride, sulfate, phosphate, acetate, propionate, lactate or citrate.

The couplers are generally used in approximately equimolar amounts with respect to the developers. Although equimolar use has proven advisable, it is not disadvantageous if the amount of couplers used exceeds or falls below that of the developers. Further, it is not necessary that the developer components and coupler components consist of only one dye. Rather, the developer component can be a mixture of known developers and the coupler component can also be a mixture of known couplers.

The known couplers contained in the hair dye composition are particularly 1-naphthol, 4-methoxy-1-naphthol, resorcinol, 4-chlororesorcinol, 4,6-dichlororesorcinol, 2-methylresorcinol, 3-aminophenol, 3-amino-6-methylphenol, 4-hydroxy-1,2-methylene-dioxybenzene, 4-amino-1,2-methylenedioxybenzene, 4-(2'-hydroxyethylamino)-1,2-methylenedioxybenzene, 4-hydroxyindole, 2,3-diamino-6-methoxypyridine, and 5-amino-2-methylphenol. Examples of other suitable couplers are 2,4-dihydroxyphenolethers such as 2,4-dihydroxyanisole and 2,4-dihydroxyphenoxyethanol.

The known developers contained in the hair dye composition according to the invention are preferably 1,4-diaminobenzene, 2,5-diaminotoluene, 2,5-diaminobenzyl alcohol, 3-methyl-4-aminophenol, 2-(2'-hydroxyethyl)-1,4-diaminobenzene, tetraaminopyrimidine, and 4-aminophenol. Known conventional oxidative dyes for dyeing hair which can be contained in the hair dye composition are described, among others, in E. Sagarin, "Cosmetics, Science and Technology", Interscience Publishers Inc., N.Y. (1957), pages 503 ff., and in H. Janistyn, "Handbook of Cosmetics and Fragrances" [Handbuch der Kosmetika und Riechstoffe] (1973), pages 388 ff.

The total amount of combined developers and couplers contained in the hair dye composition described here is approximately 0.01 to 12.0 percent by weight, particularly 0.2 to 4.0 percent by weight.

Further, conventional direct-dyeing dyes can also be contained to achieve certain shades, e.g. triphenylmethane dyes such as Diamond Fuchsine (C.I. 42,510) (4-{(4'-aminophenyl)-(4"-imino-2",5"-cyclohexadien-1"-yliden)methyl}-2-methyl-aminobenzene monohydrochloride) and Leather Ruby HF (C.I. 42,520) (4-{(4'-amino-3'-methylphenyl)-(4"-imino-3"-methyl-2",5"-cyclohexadien- 1"-yliden)methyl}-2-methylaminobenzene monohydrochloride), aromatic nitro dyes such as 2-amino-4,6-dinitrophenol, 2-nitro-4-(2'-hydroxyethylamino)aniline, 2-N-2',3'-dihydroxypropylamino-5-(N-methyl, N-hydroxyethyl)aminonitrobenzene, and 2-amino-4-nitrophenol, azo dyes such as Acid Brown 4 (C.I. 14,805) (6-{(4'-aminophenyl)azo}-5-hydroxy-naphthalin-1-sulfonic acid sodium salt) and Acid Blue 135 (C.I. 13,385) (5-hydroxy-4-{1'-(4'-phenylamino-5'-sulfonaphthyl)-azo}-naphthalin-1-sulfonic acid disodium salt), anthraquinone dyes such as Disperse Violet 4 (C.I. 61,105) (1-amino-4-methylaminoanthraquinone), Disperse Blue 1 (C.I. 64,500) (1,4, 5,8-tetraaminoanthraquinone), Disperse Red 15 (C.I. 60,710) (1-amino-4-hydroxyanthraquinone), and Disperse Violet 1 (C.I. 61,100) (1,4-diaminoanthraquinone).

Further, the hair dye composition can also contain self-coupling dye precursors such as 2-amino-5-methylphenol, 2-amino-6-methylphenol, 2-amino-5-ethoxyphenol or also 2-propylamino-5-aminopyridine.

The total amount of direct dyes and self-coupling dye precursors is 0.01 to 6 percent by weight, preferably 0.2 to 4 percent by weight.

The total amount of all dyes, that is, the combination of developers and couplers, self-coupling dye precursors and direct dyes, is 0.1 to 14 percent by weight, preferably 0.2 to 8.0 percent by weight.

The oxidizing hair dye composition according to the invention represents a mixture of the carrier substance and the dye mixture.

To apply, the hair dye composition is mixed immediately before using with an oxidizing agent in liquid or cream form containing an oxidizing ingredient in a weight ratio of 2:1 to 1:3. The oxidizing agent can also contain additional conventional additives such as emulsifiers and wetting agents, thickeners such as fatty alcohols, acids such as phosphoric acid, buffers, stabilizers such as phenacetin, cationic resins, perfume oils, acrylates and opacifiers. Hydrogen peroxide, e.g. in a 6-percent aqueous solution or its addition compounds in urea, melamine or sodium borate, are particularly suitable as oxidizing ingredients for developing the hair dye. The hydrogen peroxide is contained in the oxidizing agent in a concentration of 0.1 to 20 percent by weight, preferably 1.0 to 12 percent by weight.

The ready-to-use mixture of the hair dye composition and the oxidizing agent is applied to the hair in an amount sufficient for dyeing the hair, generally 90 to 160 g depending on the fullness of the hair, and is allowed to act on the hair at 15° to 50° C. for approximately 10 to 45 minutes, preferably 30 minutes. The hair is then rinsed with water and dried. If necessary, after rinsing the hair is rinsed again with a weak, physiologically compatible organic acid such as citric acid or tartaric acid.

In the hair dye composition according to the invention there is not a high degree of thickening as in conventional hair dye compositions in cream form, even after long storage. A further characteristic of the composition consists in that it easily forms a stable emulsion. The forming of the emulsion is effected even at relatively high temperatures so that it is possible to produce an emulsion concentrate which can be diluted subsequently with cold water. This considerably facilitates the production of hair dye compositions in cream form.

The following examples for the hair dye composition according to the invention will explain the subject matter in more detail.

| | | |
|---|---|---|
| 1. | cetyl stearyl alcohol | 16.20 g |
| 2. | sodium lauryl sulfate | 1.80 g |
| 3. | glycerin monodistearate | 7.50 g |
| 4. | glycerin | 0.80 g |
| 4a. | potassium stearate | 0.55 g |
| 5. | glycol distearate | 1.80 g |
| 6. | sodium lauryl alcohol diglycol ether sulfate, 26-percent aqueous solution | 10.00 g |
| 7. | sodium sulfite, anhydrous | 0.50 g |
| 8. | 2,5-diaminotoluene sulfate | 1.20 g |
| 9. | resorcinol | 0.50 g |
| 10. | m-aminophenol | 0.10 g |
| 11. | ammonia, 25-percent aqueous solution | 0.90 g |
| 12. | water | 52.15 g |
| 13. | ammonia, 25-percent aqueous solution | 6.00 g |
| | | 100.00 g |

Components 1 to 5 which form the wax phase are melted together at 90° C. The boiling aqueous solution containing raw materials 6 to 12 is stirred into the melt. The resulting mixture is allowed to cool accompanied by stirring and forms an emulsion easily. After cooling the cream, the pH is adjusted to 10.3 with aqueous ammonia solution (13.).

| 1. | cetyl stearyl alcohol | 13.50 g |
|---|---|---|
| 2. | sodium lauryl sulfate | 1.50 g |
| 3. | glycerin monostearate | 11.30 g |
| 4. | glycerin | 3.70 g |
| 4a. | potassium stearate | 0.82 g |
| 5. | glycol distearate | 1.80 g |
| 6. | water | 30.00 g |
| 7. | sodium lauryl alcohol diglycol ether sulfate, 26-percent aqueous solution | 10.00 g |
| 8. | sodium sulfite, anhydrous | 0.50 g |
| 9. | 2,5-diaminotoluene sulfate | 1.60 g |
| 10. | resorcinol | 0.60 g |
| 11. | 3-aminophenol | 0.20 g |
| 12. | ammonia, 25-percent aqueous solution | 1.20 g |
| 13. | water | 17.28 g |
| 14. | ammonia, 25-percent aqueous solution | 6.00 g |
| | | 100.00 g |

An aqueous solution of components 6 to 12 at a temperature of 95° C. are poured in a melt of components 1 to 5 produced at 90° C. accompanied by stirring. Water (13) is then allowed to flow into the mixture at 40°–60° C. causing a more rapid cooling. The emulsion forms smoothly. The pH is adjusted to 10.0 with aqueous ammonia solution (14).

| 1. | cetyl stearyl alcohol | 18.45 g |
|---|---|---|
| 2. | sodium lauryl sulfate | 2.05 g |
| 3. | glycerin monostearate | 4.90 g |
| 4. | glycerin | 1.60 g |
| 4a. | potassium stearate | 0.36 g |
| 5. | cholesterol | 0.60 g |
| 6. | glycol distearate | 1.80 g |
| 7. | cetyl alcohol polyethylene glycol ether | 2.00 g |
| 8. | sodium lauryl alcohol diglycol ether sulfate, 26-percent aqueous solution | 10.00 g |
| 9. | ascorbic acid | 0.30 g |
| 10. | resorcinol | 0.30 g |
| 11. | 2,5-diaminotoluene sulfate | 0.60 g |
| 12. | ammonia, 25-percent aqueous solution | 6.00 g |
| 13. | water | 51.04 g |
| | | 100.00 g |

After components 1 to 6 have been melted together at 90° C., the emulsion is produced as described in Example 1. 50 g of the hair dye cream are mixed shortly before use with 50 g 6 percent hydrogen peroxide emulsion of the following composition:

| cetyl stearyl alcohol | 2.00 g |
|---|---|
| sodium lauryl sulfate | 0.28 g |
| cetyl alcohol polyethylene glycol ether | 0.10 g |
| hydrogen peroxide, 50-percent solution | 12.00 g |
| phosphoric acid, 85-percent solution | 0.10 g |
| water | 85.62 g |
| | 100.00 g |

The mixture is then applied to graying human hair and allowed to act for a period of thirty minutes at room temperature. The hair is then rinsed with water and dried. The hair is dyed light blond.

Comparison examples

Hair dye compositions according to Examples 1 to 3 were compared with hair dye compositions of the same composition, but in which the glycol distearate was replaced by an equal amount of water (Examples 1A, 2A and 3A).

In contrast to the composition according to the invention in Example 1, Example 1A formed a poor emulsion. It is unstable and tends to form clumps and separate in phases periodically. While the dye carrier substance according to the invention in Example 2 forms a stable emulsion without difficulty, a separation of phases occurs in Example 2A which contains no glycol diester.

Both the hair dye cream according to Example 3 and the corresponding hair dye cream which is not part of the invention (Example 3A) are placed in tubes after production and stored for approximately ten days. When removed from the tube, the dye substance with no glycol distearate (Example 3A) shows subsequent thickening and is clearly more stringy than the hair dye cream according to the invention (Example 3).

All percentages are percentage by weight unless otherwise indicated.

We claim:

1. Composition for oxidative dyeing of hair in the form of a cream and consisting of a carrier substance and a dye mixture dissolved therein, said dye mixture containing at least one coupler and at least one developer, and said composition having a pH of 4.5 to 12.5 and, in addition to said dye mixture, consisting essentially of:

(A) 10 to 30 percent by weight of at least one fatty alcohol with 10 to 24 carbon atoms, (B) 0.2 to 6.0 percent by weight of at least one diester of the following formula $$R_1\text{—CO—O—}(CH_2\text{—}CH_2\text{—O})_n\text{—CO—}R_2 \qquad (I),$$

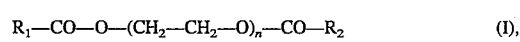

where n is 1, 2 or 3, and $R_1$ and $R_2$ are each independently selected from the group consisting of alkyl groups with 12 to 20 carbon atoms, (C) 0.5 to 20 percent by weight glycerin fatty acid ester with 10 to 24 carbon atoms, and (D) 0.1 to 10 percent by weight of at least one emulsifier member selected from the group consisting of nonionic emulsifiers, anionic emulsifiers and ampholytic emulsifiers;

and in addition the total content of said at least one fatty alcohol, said at least one diester and said glycerin fatty acid ester is from 25.0 to 56.0 percent by weight, all weights being based on the total weight of the composition.

2. Composition according to claim 1, wherein said at least one diester comprises ethylene glycol distearate.

3. Composition according to claim 1, wherein said glycerin fatty acid ester comprises glycerin monostearate.

4. Composition according to claim 3, containing 0.5 to 10.0 percent by weight of the glycerin monostearate.

5. Composition according to claim 1, wherein said at least one emulsifier member includes sodium lauryl alcohol diglycol ether sulfate as a major portion thereof.

6. Composition according to claim 1, wherein said at least one coupler is selected from the group consisting of 1-naphthol, 4-methoxy-1-naphthol, resorcinol, 4-chlororesorcinol, 4,6-dichlororesorcinol, 2-methylresorcinol, 3-aminophenol, 3-amino-6-methylphenol, 4-hydroxy-1,2-methylenedioxybenzene, 4-hydroxyindole, 2,4-dihydroxyanisole and 2,4-dihydroxyphenoxyethanol.

7. Composition according to claim 1, wherein said at least one developer is selected from the group consisting of 2,5-diaminotoluene, 3-methyl-4-aminophenol, 1,4-diaminobenzene, 2-(2'-hydroxyethyl)-1,4-diaminobenzene, tetraaminopyrimidine and 4-aminophenol.

8. Composition according to claim 1, wherein said dye mixture additionally contains at least one direct dye selected from the group consisting of 4-{(4'-aminophenyl)-(4"-imino-2",5"-cyclohexadien-1"-yliden)methyl}-2-methyl-aminobenzene monohydrochloride, 4-{(4'-amino-3'-methylphenyl)-(4"-imino-3"-methyl-2",5"-cyclohexadien-1"-yliden)methyl}-2-methyl-aminobenzene monohydrochloride, 2-amino-4,6-dinitrophenol, 2-nitro-4-(2'-hydroxyethylamino)aniline, 2-N-2',3'-dihydroxypropylamino-5-(N-methyl, N-hydroxyethyl)aminonitrobenzene, 2-amino-4-nitrophenol, 6-{(4'-aminophenyl)azo}-5-hydroxy-naphthalin-1-sulfonic acid sodium salt, 5-hydroxy-4-{1'-(4'-phenylamino-5'-sulfonaphthyl)azo}-naphthalin-1-sulfonic acid disodium salt, 1-amino-4-methylaminoanthraquinone, 1-amino-4-hydroxyanthraquinone, 1,4,5,8-tetraaminoanthraquinone and 1,4-diaminoanthraquinone.

9. Process for oxidative dyeing of hair comprising the steps of:

a) mixing the hair dye composition according to claim 1 with an oxidizing agent containing an oxidizing ingredient to form a hair dyeing mixture;

b) immediately after said mixing in step a), applying an amount of said hair dyeing mixture sufficient for treating the hair;

c) allowing said hair dyeing mixture to act on the hair treated in step b) for 10 to 45 minutes at 15° to 50° C.; and d) after said allowing the hair dyeing mixture to act on the hair in step c), rinsing said hair dyeing mixture from the hair and drying the hair.

10. Process as defined in claim 9, wherein said oxidizing agent is hydrogen peroxide.

* * * * *